US010769789B2

United States Patent
Kotoku et al.

(10) Patent No.: US 10,769,789 B2
(45) Date of Patent: Sep. 8, 2020

(54) IMAGE PROCESSING APPARATUS AND IMAGE PROCESSING METHOD

(71) Applicant: CANON KABUSHIKI KAISHA, Tokyo (JP)

(72) Inventors: Masashi Kotoku, Yokohama (JP); Yoshihiko Iwase, Yokohama (JP); Makoto Sato, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 312 days.

(21) Appl. No.: 15/495,660

(22) Filed: Apr. 24, 2017

(65) Prior Publication Data

US 2017/0316567 A1    Nov. 2, 2017

(30) Foreign Application Priority Data

Apr. 28, 2016  (JP) .................................. 2016-091607

(51) Int. Cl.
*G06T 7/00*    (2017.01)
*G06T 7/11*    (2017.01)
(Continued)

(52) U.S. Cl.
CPC ............ *G06T 7/0016* (2013.01); *A61B 3/102* (2013.01); *G06T 7/0012* (2013.01); *G06T 7/11* (2017.01);
(Continued)

(58) Field of Classification Search
CPC ....... G06T 7/0016; G06T 7/11; G06T 7/0012; G06T 11/00; A61B 3/102
See application file for complete search history.

(56) References Cited

U.S. PATENT DOCUMENTS 8,208,996 B2 * 6/2012 Meyer .................... A61B 3/102
356/364
8,857,988 B2 * 10/2014 Sharma .................. A61B 3/102
351/206
(Continued)

FOREIGN PATENT DOCUMENTS

JP    2008-513067 A    5/2008
JP    2008-154704 A    7/2008
(Continued)

OTHER PUBLICATIONS

Jeff Fingler et al.; "Mobility and transverse flow visualization using phase variance contrast with spectral domain optical coherence tomography;" Oct. 1, 2007 / Optics Express, vol. 15, No. 20, pp. 12637-12653.

(Continued)

*Primary Examiner* — Kim Y Vu
*Assistant Examiner* — Molly Delaney
(74) *Attorney, Agent, or Firm* — Canon U.S.A., Inc. IP Division (57) ABSTRACT

An image processing apparatus includes an information obtaining unit configured to obtain three-dimensional polarization sensitive tomographic information and three-dimensional motion contrast information about a subject based on tomographic signals of lights having different polarizations, the lights being obtained by splitting a combined light obtained by combining a returned light from the subject illuminated with a measurement light with a reference light corresponding to the measurement light, an obtaining unit configured to obtain a lesion region of the subject using the three-dimensional polarization sensitive tomographic information, and an image generation unit configured to generate an image in which the lesion region is superimposed on a (Continued)

motion contrast image generated using the three-dimensional motion contrast information.

18 Claims, 7 Drawing Sheets

(51) Int. Cl.
*G06T 15/08* (2011.01)
*G06T 11/00* (2006.01)
*G06T 19/00* (2011.01)
*A61B 3/10* (2006.01)

(52) U.S. Cl.
CPC .............. *G06T 11/00* (2013.01); *G06T 15/08* (2013.01); *G06T 19/00* (2013.01); *G06T 2207/10101* (2013.01); *G06T 2207/10141* (2013.01); *G06T 2207/20221* (2013.01); *G06T 2207/30041* (2013.01); *G06T 2207/30096* (2013.01); *G06T 2207/30104* (2013.01); *G06T 2210/41* (2013.01); *G06T 2211/404* (2013.01)

(56) References Cited

U.S. PATENT DOCUMENTS

| | | | |
|---|---|---|---|
| 9,545,196 B2* | 1/2017 | Abramoff | A61B 3/102 |
| 9,700,206 B2* | 7/2017 | An | A61B 3/1233 |
| 9,713,424 B2* | 7/2017 | Spaide | G06T 15/08 |
| 9,826,900 B2* | 11/2017 | Heeren | A61B 3/12 |
| 9,955,863 B2* | 5/2018 | Frisken | A61B 3/0025 |
| 10,022,047 B2* | 7/2018 | Yamashita | A61B 3/102 |
| 10,136,806 B2* | 11/2018 | Sumiya | A61B 3/0025 |
| 10,152,807 B2* | 12/2018 | Kuno | G06T 11/008 |
| 2011/0129133 A1 | 6/2011 | Ramos | |
| 2014/0221827 A1 | 8/2014 | Motaghiannezam | |
| 2016/0227999 A1* | 8/2016 | An | A61B 3/1233 |

FOREIGN PATENT DOCUMENTS

| | | | | |
|---|---|---|---|---|
| JP | 2013-542840 A | | 11/2013 | |
| JP | 2014-083285 A | | 5/2014 | |
| JP | 2014-110884 A | | 6/2014 | |
| JP | 2016-010657 A | | 1/2016 | |
| JP | 2017006179 A | * | 1/2017 | .......... G06T 11/008 |
| WO | WO-2016187675 A1 | * | 12/2016 | .......... A61B 3/0025 |

OTHER PUBLICATIONS

Stefan Zotter et al.; "Measuring retinal nerve fiber layer birefringence, retardation, and thickness using wide-field, high-speed polarization sensitive spectral domain OCT;" Investigative Ophthalmology & Visual Science, Jan. 2013, vol. 54, No. 1, pp. 72-84.

* cited by examiner

IMAGE PROCESSING APPARATUS AND IMAGE PROCESSING METHOD

BACKGROUND

Field of the Disclosure

The present disclosure relates to an image processing apparatus and image processing method for processing an image of a subject.

Description of the Related Art

Optical coherence tomography (hereinafter referred to OCT) has been used as a non-destructive and non-invasive method for obtaining a tomographic image of a measurement target, such as a living body. OCT is widely used especially in the field of ophthalmology to obtain tomographic images of a retina in a fundus of an eye to be examined for ophthalmic examination of the retina and the like.

In OCT, light reflected from a measurement target interferes with light reflected from a reference mirror, and the time- or wavenumber-dependence of the intensity of the interfering light is analyzed to obtain tomographic images. Examples of a known apparatus for obtaining such an OCT image include a time domain OCT, a spectral domain OCT (SD-OCT), and a swept source OCT (SS-OCT). The time domain OCT obtains depth information about a measurement target by moving a reference mirror to different positions. The SD-OCT uses a broad-bandwidth light source. The SS-OCT uses as a light source a wavelength-tunable light source in which an oscillation wavelength is tunable. The SD-OCT and the SS-OCT are collectively referred to as Fourier domain OCT (FD-OCT).

In recent years, a virtual angiography using FD-OCT has been discussed, and such virtual angiography is called OCT angiography (OCTA). A fluorescein angiography, which is a commonly-used angiography in modern clinical practice, requires injection of a fluorescent dye (e.g., fluorescein or indocyanine green) into a body and produces a two-dimensional representation of blood vessels through which the fluorescent dye passes. On the other hand, the OCTA enables a non-invasive virtual angiography and can provide a three-dimensional representation of a network of blood flow. Furthermore, the OCTA has a higher resolution than the fluorescein angiography and can produce images of fine blood vessels or blood flow in the eye fundus. For this reason, the OCTA has been attracting rising attention.

A method of detecting blood flow with the OCTA is discussed in Fingler et al. "Mobility and transverse flow visualization using phase variance contrast with spectral domain optical coherence tomography", Optics Express, Vol. 15, No. 20, pp 12637-12653 (2007). In the method discussed therein, only time-modulated signals are extracted from OCT signals to separate the OCT signals that are from blood flow. Other methods for detecting blood flow are also discussed including a method which uses intensity fluctuations due to blood flow (United States Patent Application Publication No. 2014/221827) and a method which uses phase fluctuations due to blood flow. As used herein, an image showing time-modulated signals which are signals among OCT signals is sometimes referred to as a "motion contrast image", a pixel value of the motion contrast image as "motion contrast", and a data set of the motion contrast as "motion contrast data".

Meanwhile, a polarization OCT developed as a functional OCT is capable of visualizing structural information, such as a nerve fiber layer and a retinal layer. Investigative Ophthalmology & Visual Science, Jan. 7, 2013, Zotter S et al., "Measuring retinal nerve fiber layer birefringence, retardation, and thickness using wide-field, high-speed polarization sensitive spectral domain OCT" discusses a technique for obtaining en face maps using the polarization OCT by integrating, along a thickness direction, three-dimensional data per unit thickness on a retinal nerve fiber layer (RNFL) deflection parameter called retardation.

SUMMARY

According to an aspect of the present invention, an image processing apparatus includes an information obtaining unit configured to obtain three-dimensional polarization sensitive tomographic information and three-dimensional motion contrast information about a subject based on tomographic signals of lights having different polarizations, the lights obtained by splitting a combined light obtained by combining a returned light from the subject illuminated with a measurement light with a reference light corresponding to the measurement light, an obtaining unit configured to obtain a lesion region of the subject using the three-dimensional polarization sensitive tomographic information, and an image generation unit configured to generate an image in which the lesion region is superimposed on a motion contrast image generated using the three-dimensional motion contrast information.

Further features of the present invention will become apparent from the following description of exemplary embodiments with reference to the attached drawings.

DESCRIPTION OF THE EMBODIMENTS

In age-related macular degeneration (AMD) involving development of new blood vessels, the new blood vessels which are characteristic of AMD grow rapidly after developing from the choroid, breaking through the Bruch's membrane, and forming underneath or above the retinal pigment epithelium (RPE). A leakage of blood from the new blood vessels causes distortion of vision and formation of fibrotic tissues around the leakage point. In order to provide appropriate treatment to a patient with AMD involving development of new blood vessels, the new blood vessels and fibrotic tissues (fibrosis) need to be discriminated from each other and identified. Because, for example, to the blood leakage from the new blood vessels, administration of a drug which inhibits a vascular endothelial growth factor (VEGF) can inhibit the growth of the new blood vessels but is not likely to have an effect on tissues that are already fibrotic. Further, in order to determine the effect of the treatment, it is necessary to identify changes in the respective tissues over time.

However, in conventional OCT luminance images, it is difficult to discriminate between RPE, fibrotic tissues, and new blood vessels because all of them appear as similar high luminance reflection regions. Further, with OCTA or polarization OCT alone, it is difficult to comprehensively identify tissues associated with the development of AMD. Further, it is also difficult to identify temporal or spatial changes in the tissues. Thus, it has been difficult to find out the development of the disease.

The present invention is directed to a technique for generating an image in which tissues that are difficult to identify, such as new blood vessels and fibrotic tissues, are identifiable.

An imaging apparatus according to an exemplary embodiment of the present invention will be described below with reference to the drawings. Configurations and processes described in the below-described exemplary embodiment are mere examples and are not intended to limit the scope of the invention. Further, while a subject is a human eye (fundus) in the present exemplary embodiment, the subject is not limited to the human eye (fundus) and can be, for example, skin. Further, while an imaging target is the fundus of an eye in the present exemplary embodiment, the imaging target can be an anterior eye.

<Configuration of Polarization OCT Apparatus>

Figure 1:
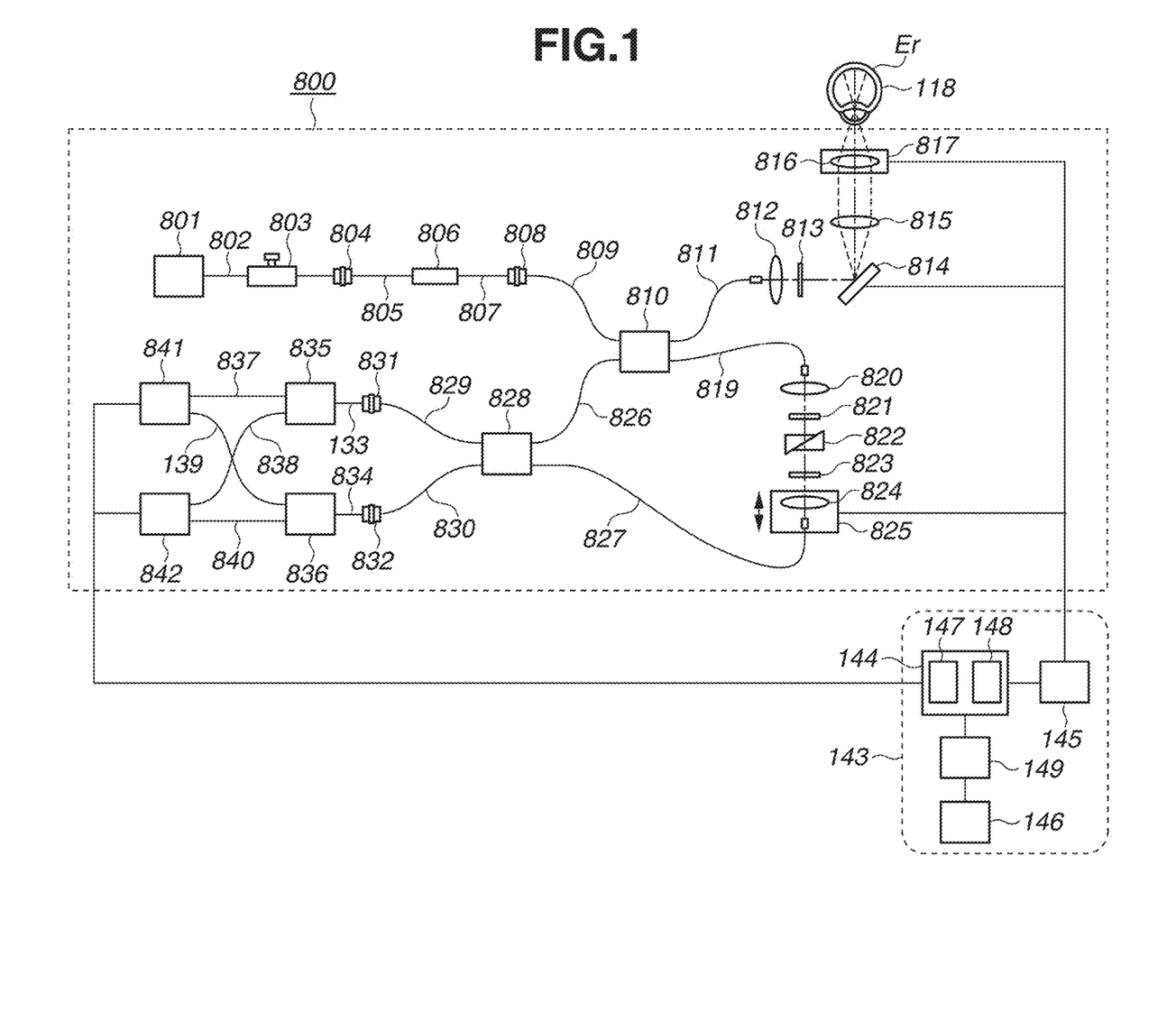
FIG. 1 is a schematic diagram illustrating an example of an entire configuration of an apparatus according to an exemplary embodiment of the present invention.

FIG. 1 illustrates an example of a configuration of an image processing apparatus according to an exemplary embodiment of the present invention. In the present exemplary embodiment, a polarization OCT apparatus using SS-OCT will be described. The present exemplary embodiment is also applicable to a polarization OCT apparatus using SD-OCT. An apparatus according to the present exemplary embodiment includes an OCT image obtaining unit 800 configured to obtain OCT signals and a control unit 143. The OCT image obtaining unit 800 is an example of an imaging apparatus, and the control unit 143 is an example of the image processing apparatus according to the present exemplary embodiment. The OCT image obtaining unit 800 and the control unit 143 are connected to communicate with each other. Alternatively, the control unit 143 can be built in and integrated with the imaging apparatus. The control unit 143 includes a signal processing unit 144, a signal obtaining control unit 145, a display control unit 149, and a display unit 146. The signal processing unit 144 includes an image generation unit 147 and a map generation unit 148.

First, a configuration of the OCT image obtaining unit 800 will be described. A light source 801 is a swept source (SS) light source which emits light while sweeping at, for example, a sweep central wavelength of 1050 nm and a sweep width of 100 nm. The light emitted from the light source 801 is guided to a beam splitter 810 via a single mode fiber (hereinafter, "SM fiber") 802, a polarization control device 803, a connector 804, a SM fiber 805, a polarizer 806, a polarization maintaining (PM) fiber (hereinafter, "PM fiber") 807, a connector 808, and a PM fiber 809, and split into measurement light (also referred to as "OCT measurement light") and reference light (also referred to as "reference light corresponding to OCT measurement light"). The splitting ratio of the beam splitter 810 is 90 (reference light):10 (measurement light). The polarization control device 803 can change polarization of the light emitted from the light source 801 into a desired polarization state. The polarizer 806 is an optical element having the characteristic that it transmits only specific linearly-polarized components. In general, the light emitted from the light source 801 has a high degree of polarization, and a majority of the light has a specific polarization direction, but the light also includes light having no specific polarization direction, which is called randomly-polarized components. The randomly-polarized components are known to impair the image quality of polarization OCT images, so the polarizer 806 cuts the randomly-polarized components. Only light that is in a specific linearly-polarized state can pass through the polarizer 806, so the polarization control device 803 adjusts the polarization state such that a desired amount of light enters an eye to be examined 118.

The split measurement light is output via a PM fiber 811 and then changed into parallel light by a collimator 812. The measurement light changed to the parallel light passes through a quarter-wave plate 813 and then enters the eye to be examined 118 via a galvano scanner 814, a scan lens 815, and a focusing lens 816. The galvano scanner 814 is a scanner which scans a fundus Er of the eye to be examined 118 with the measurement light. While the galvano scanner 814 is described above as a single mirror, the actual galvano scanner 814 includes two galvano scanners perform raster scanning on the fundus Er of the eye to be examined 118. Further, the focusing lens 816 is fixed onto a stage 817 and is moved along an optical axis direction to adjust a focus. The galvano scanner 814 and the stage 817 are controlled by the signal obtaining control unit 145, and a desired range (also referred to as "tomographic image obtaining range", "tomographic image obtaining position", "measurement light illumination position") of the fundus Er of the eye to be examined 118 can be scanned with the measurement light. Further, the quarter-wave plate 813 is an optical element having the characteristic that it delays by a quarter wavelength a phase between an optical axis of the quarter-wave plate 813 and an axis which is orthogonal to the optical axis. In the present exemplary embodiment, the optical axis of the quarter-wave plate 813 is rotated about the optical axis by degrees with respect to the direction of the linear polarization of the measurement light emitted from the PM fiber 811 so that circularly polarized light enters the eye to be examined 118. While details are not described in the present exemplary embodiment, a tracking function is desirably provided. The tracking function is a function with which the movement of the fundus Er is detected and the mirror of the galvano scanner 814 follows the movement of the fundus Er to scan the fundus Er. The tracking can be performed using a commonly-used technique, either in real time or post-processing. Examples include a method using a scanning laser ophthalmoscope (SLO). In this method, two-dimensional images of a plane of the fundus Er which is vertical to the optical axis are obtained over time with the SLO, and a feature portion such as a vascular bifurcation in the images is obtained. Then, how the feature point in the obtained two-dimensional images is moved is calculated as an amount of movement of the fundus Er, and the calculated amount of movement is fed back to the galvano scanner 814 to perform real-time tracking.

The measurement light is caused to enter the eye to be examined 118 and is focused onto the fundus Er by the focusing lens 816 placed on the stage 817. The measurement light illuminating the fundus Er is reflected and scattered by each retinal layer and then returns through the above-described optical path to the beam splitter 810. The returned light of the measurement light having entered the beam splitter 810 passes through a PM fiber 826 and enters a beam splitter 828.

On the other hand, the reference light split at the beam splitter 810 is output via a PM fiber 819 and then changed into parallel light by a collimator 820. The reference light enters a PM fiber 827 via a half-wave plate 821, a dispersion compensation glass 822, a ND filter 823, and a collimator 824. The collimator 824 and one end of the PM fiber 827 are fixed onto a coherence gate stage 825 and are controlled by the signal obtaining control unit 145 to drive along the optical axis direction correspondingly to a difference in axial length of the eye of an examinee, etc. The half-wave plate 821 is an optical element having the characteristic that it delays by a half wavelength a phase between the optical axis of the half-wave plate 821 and an axis which is orthogonal to the optical axis. In the present exemplary embodiment, an adjustment is made such that the linear polarization of the reference light output from the PM fiber 819 is in a polarization state in which a longer axis is inclined by 45 degrees at the PM fiber 827. While the optical length of the reference light is changed in the present exemplary embodiment, any method to change the difference in optical length between the optical paths of the measurement light and the reference light can be employed.

The reference light having passed through the PM fiber 827 enters the beam splitter 828. The beam splitter 828 combines the returned light of the reference light with the reference light to obtain combined light (interfering light) and then splits the combined light into two. The split interfering light beams have opposite phases to each other (hereinafter, "positive and negative components"). The positive component of the split interfering light passes through a PM fiber 829, a connector 831, and a PM fiber 833 and then enters a polarization beam splitter 835. On the other hand, the negative component of the interfering light passes through a PM fiber 830, a connector 832, and a PM fiber 834 and then enters a polarization beam splitter 836.

The polarization beam splitters 835 and 836 split the interfering light along two orthogonal polarization axes into two, which are a vertically-polarized component (hereinafter, "V-polarized component") and horizontally-polarized component (hereinafter, "H-polarized component"). The positive interfering light having entered the polarization beam splitter 835 is split by the polarization beam splitter 835 into two, which are a positive V-polarized component and positive H-polarized component. The split positive V-polarized component passes through a PM fiber 837 and enters a detector 841, and the split positive H-polarized components passes through a PM fiber 838 and enters a detector 842. On the other hand, the negative interfering light having entered the polarization beam splitter 836 is split by the polarization beam splitter 836 into a negative V-polarized component and negative H-polarized component. The negative V-polarized component passes through a PM fiber 139 and then enters the detector 841, and the negative H-polarized component passes through a PM fiber 840 and then enters the detector 842.

Each of the detectors 841 and 842 is a difference detection device. When two interference signals having phases inverted by 180 degrees are input, the detectors 841 and 842 remove direct current components and output only interference components.

The V-polarized components of the interference signals detected by the detector 841 and the H-polarized components of the interference signals detected by the detector 842 are respectively output as electric signals corresponding to light intensity and input to the signal processing unit 144, which is an example of a tomographic image generation unit.

<Scan Pattern>

As used herein, "A-scan" refers to obtaining of information about a tomographic image of the eye to be examined 118 along a depth direction. Further, "B-scan" refers to a scan for obtaining of information about a tomographic image of the eye to be examined 118 along a direction that is orthogonal to the scanning direction of the A-scan, i.e., a scan for obtaining a two-dimensional image. Further, "C-scan" refers to a scan in a direction that is orthogonal to the tomographic image obtained by the B-scan. Specifically, in two-dimensional raster scanning within a fundus plane during obtaining of a three-dimensional tomographic image, the B-scan refers to a high-speed scanning direction, and the C-scan refers to a low-speed scanning direction in which the B-scans are arranged in the orthogonal direction. By performing the A- and B-scans, a two-dimensional tomographic image is obtained. By performing the A-, B-, and C-scans, a three-dimensional tomographic image is obtained. The B- and C-scans are performed by the galvano scanner 114.

An X-axis scanner 114a (not illustrated) and a Y-axis scanner 114b (not illustrated) respectively include deflection mirrors located such that rotation axes of the deflection mirrors are orthogonal to each other. The X-axis scanner 114a performs scans in an X-axis direction, and the Y-axis scanner 114b performs scans in a Y-axis direction. Each of the X-axis and Y-axis directions is vertical to an eye axis direction of the eyeball, and the X-axis and Y-axis directions are vertical to each other. Further, the direction of a line scan, such as the B- or C-scan, does not have to match the X-axis or Y-axis direction. Thus, the direction of the line scan, such as the B- or C-scan, can be determined as appropriate to a two- or three-dimensional tomographic image to be captured.

Figure 2:
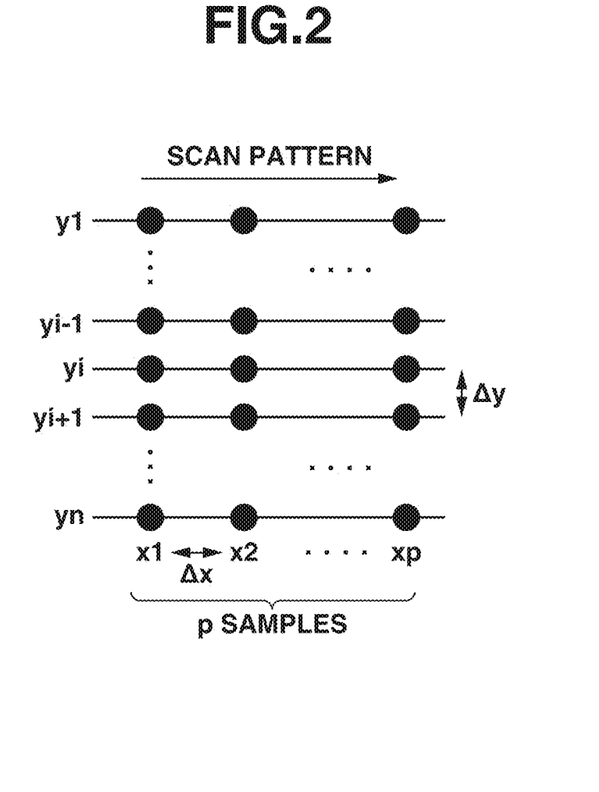
FIG. 2 is a diagram illustrating an example of scan patterns according to an exemplary embodiment of the present invention.

Next, an example of a scan pattern according to the present exemplary embodiment will be described below with reference to FIG. 2. In OCT angiography, changes over time in OCT interference signals by blood streams are measured, so the measurement needs to be performed a plurality of times at the same position (or substantially the same position). In the present exemplary embodiment, the OCT apparatus repeats B-scans m times at the same position while moving to n y-positions. FIG. 2 illustrates a specific scan pattern. On the fundus plane, B-scans are repeated m times in each of n y-positions y1 to yn. The larger the value of m is, the larger the number of times the measurement is performed at the same position becomes, and accuracy of blood stream detection increases. However, in such a case, the scan time increases, and this can cause a problem that a motion artifact occurs in an image due to eye movement (involuntary eye movement) during the scans and a problem that the burden on an examinee increases. In the present exemplary embodiment, the balance between the advantage and disadvantage is considered, and the value of m is set to m=4. The control unit 143 can change the value of m according to an A-scan rate of the OCT apparatus and motion analysis of a fundus surface image of the eye to be examined 118.

In FIG. 2, p indicates the number of sampling of A-scans in one B-scan. Specifically, the plane image size is determined by p×n. The larger the value of p×n is, the wider the scan range at the same measurement pitch becomes, but the scan time increases, and the problems of the motion artifact and the burden on the patient arise. In the present exemplary embodiment, the balance between the advantage and disadvantage is considered, and n and p are set to n=p=300. The values of n and p can be changed as appropriate.

Further, in FIG. 2, Δx is an interval (x-pitch) between adjacent x-positions, and Δy is an interval (y-pitch) between adjacent y-positions. In the present exemplary embodiment, the x- and y-pitches are set to ½ of a beam spot diameter of illumination light on the fundus, i.e., 10 μm. By setting the x- and y-pitches to ½ of the beam spot diameter on the fundus, a high-definition image can be generated. However, setting the x- and y-pitches smaller than ½ of the beam spot diameter on the fundus has little effect in further increasing the definition of a generated image.

On the other hand, setting the x- and y-pitches larger than ½ of the beam spot diameter on the fundus decrease the definition, but an image of a wider range can be obtained with a small data amount. The x- and y-pitches can be changed freely according to a clinical need.

<Configuration of Control Unit 143>

The following describes a configuration and function of the control unit 143 for controlling the entire apparatus. The control unit 143 includes the signal processing unit 144, the signal obtaining control unit 145, the display unit 146, and the display control unit 149. Further, the signal processing unit 144 includes the image generation unit 147 and the map generation unit 148. The signal processing unit 144 is an example of an information obtaining unit which obtains three-dimensional polarization sensitive tomographic information and three-dimensional motion contrast information on a subject. Further, the image generation unit 147 has a function of generating a luminance image and a motion contrast image from electric signals (interference signals) transmitted from the detectors 841 and 842, and the map generation unit 148 has a function of generating layer information (segmentation of retina) from the luminance image.

Further, the image generation unit 147 has a function of generating a polarization property image from electric signals transmitted to the signal processing unit 144, and the map generation unit 148 has a function of generating a fibrotic tissue image.

The signal obtaining control unit 145 controls the respective components as described above. The signal processing unit 144 generates an image based on the signals output from the detectors 841 and 842, analyzes the generated image, and generates analysis result visualization information.

The image and the analysis result information generated by the signal processing unit 144 are transmitted to the display control unit 149, and the display control unit 149 displays the image and the analysis result on a display screen of the display unit 146. The display unit 146 is, for example, a liquid crystal display. The image data generated by the signal processing unit 144 can be transmitted to the display control unit 149 and then transmitted via wires or wirelessly to the display unit 146. Further, while the display unit 146 and the like are included in the control unit 143 in the present exemplary embodiment, the present exemplary embodiment is not limited to this configuration, and the display unit 146 and the like can be provided separately from the control unit 143 and can be, for example, a tablet which is an example of an apparatus movable by an examiner. In this case, the display unit 146 desirably includes a touch panel function to enable operations on the touch panel for moving the display position of an image, enlarging or reducing the image, changing the displayed image, etc.

<Signal Processing>

Figure 3:
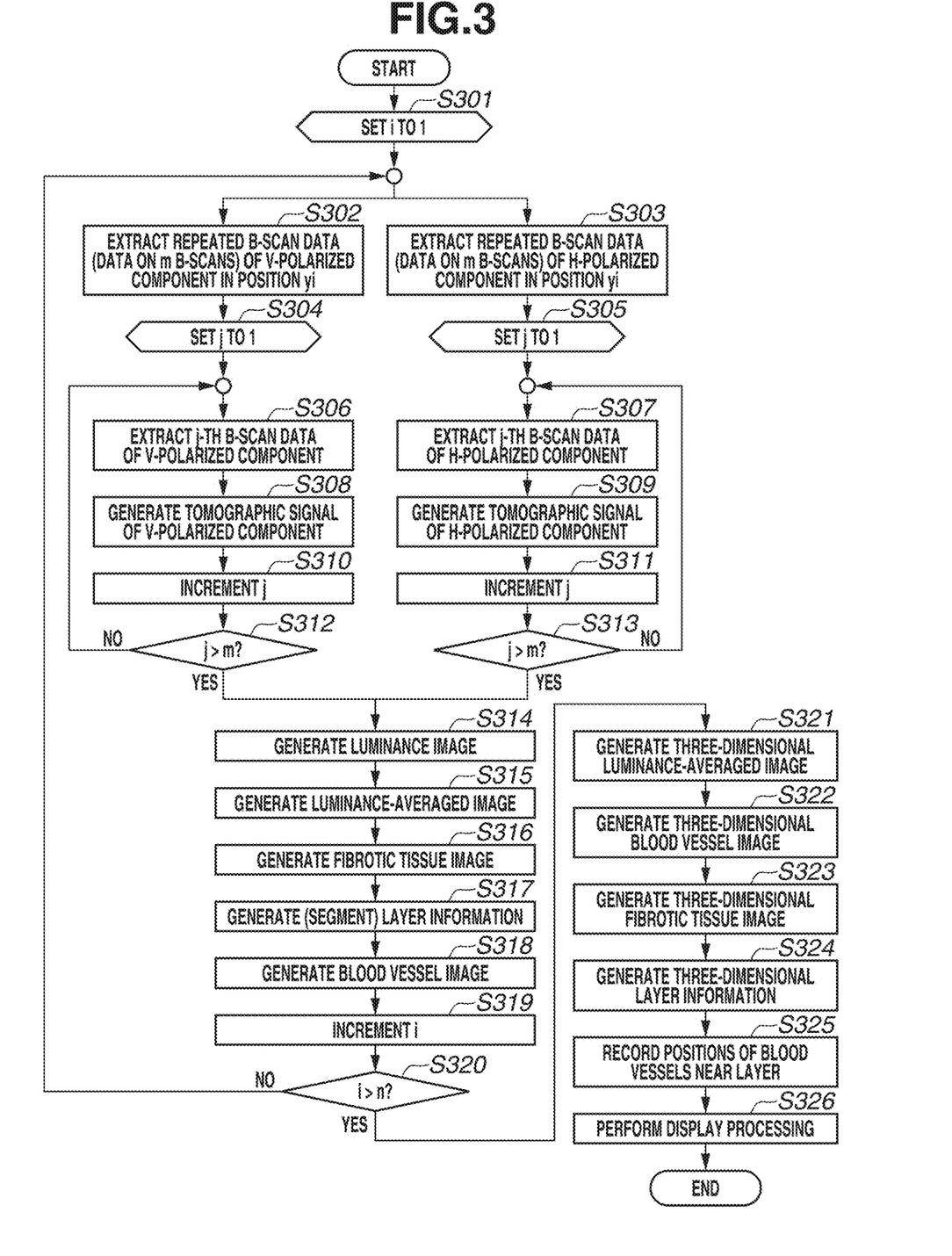
FIG. 3 is a diagram illustrating an example of a signal processing procedure according to an exemplary embodiment of the present invention.

The following describes main signal processing performed by the control unit 143, with reference to FIG. 3.

[Generation of Tomographic Signal for Each Polarization Component]

In step S301, the signal processing unit 144 sets an index i of a position yi to one. In steps S302 and S303, the signal processing unit 144 extracts repeated B-scan data (data on m B-scans) of each of the V- and H-polarized components, which are respectively output from the detectors 841 and 842, in the position yi. In steps S304 and S305, the signal processing unit 144 sets an index j of the repeat B-scan to one. In steps S306 and S307, the signal processing unit 144 extracts j-th (1≤j≤m) B-scan data of each of the V- and H-polarized components.

In steps S308 and S309, the image generation unit 147 performs commonly-used reconstruction processing on each of the B-scan data of the V-polarized component and the B-scan data of the H-polarized component extracted by the signal processing unit 144 in steps S306 and S307. Specifically, the image generation unit 147 performs on each of the B-scan data of the V-polarized component and the B-scan data of the H-polarized component the following processing. First, the image generation unit 147 removes fixed pattern noise from the B-scan data. Specifically, a plurality of pieces of A-scan data obtained with the galvano scanner 814 moved to a position such that the measurement light does not enter the eye to be examined 118 is averaged to extract fixed pattern noise, and the extracted fixed pattern noise is subtracted from the input B-scan data to remove the fixed pattern noise. Next, the image generation unit 147 performs desired window function processing to optimize a depth resolution and dynamic range, which are in a tradeoff relationship when Fourier transformed in a finite interval. Thereafter, fast Fourier transformation (FFT) processing is performed to generate tomographic signals. By the above-described processing, two tomographic signals, i.e., a tomographic signal $A_V$ of the V-polarized component and a tomographic signal $A_H$ of the H-polarized component, and a phase difference $\Delta\Phi$ between the tomographic signals $A_V$ and $A_H$ are generated.

In steps S310 and S311, the signal processing unit 144 increments the index j of the repeat B-scan. In steps S312 and S313, the signal processing unit 144 determines whether the index j is larger than the value of m. Specifically, the signal processing unit 144 determines whether the luminance calculation of the B-scan in the position yi is repeated m times. If the signal processing unit 144 determines that the index j is not larger than the value of m (NO in step S312, S313), the processing returns to steps S306 and S307, and the luminance calculation of the repeated B-scans in the same Y-position is repeated. Specifically, the image generation unit 147 obtains a plurality of tomographic signals (tomographic images) of the H- and V-polarized components of the subject which represent tomographic images of substantially the same portion of the subject.

[Generation of Luminance Image]

On the other hand, in steps S312 and S313, if the signal processing unit 144 determines that the index j is larger than the value of m (YES in step S312, S313), the processing proceeds to step S314, and the image generation unit 147 generates a luminance image.

The luminance image is basically the same as a tomographic image in conventional OCT, and a pixel value r of the luminance image is calculated from the tomographic signals $A_H$ and $A_V$ of the H- and V-polarized components using the following formula (1):

$$r=\sqrt{A_H^2+A_V^2} \qquad (1).$$

[Generation of Luminance-Averaged Image]

In step S315, the image generation unit 147 performs positioning of the luminance images of the repeated B-scans (m frames) in the yi-position to generate a luminance-averaged image.

Specifically, first, the image generation unit 147 selects any one of the m frames as a template. The template frame can be selected by calculating correlations of all combinations and calculating a sum of correlation coefficients for each frame to select a frame with the largest sum as the template frame. Next, the image generation unit 147 compares each frame with the template to calculate position gap amounts ($\delta X$, $\delta Y$, $\delta \theta$). Specifically, the image generation unit 147 calculates a normalized cross-correlation (NCC), which is an index indicating similarity, while changing the position and angle of the template image, and determines as the position gap amount a difference between image positions at the maximum NCC value.

In the present exemplary embodiment, the index indicating the similarity can be changed to any one of various measures which indicate the similarity between features of the template and the image in the frame.

Next, the image generation unit 147 applies positional correction to the m−1 frames other than the template according to the position gap amounts ($\delta X$, $\delta Y$, $\delta \theta$) to register the m frames.

The registered luminance images $r_i (1 \le i \le m)$ are averaged using the following formula (2) to generate a luminance-averaged image $\bar{r}$:

$$\bar{r} = \frac{1}{m}\sum_{i=1}^{m} r_i. \qquad (2)$$

[Generation of Fibrotic Tissue Image]

In step S316, the image generation unit 147 obtains images of a high-birefringence region and a polarization-maintained region from the tomographic image data of the H- and V-polarized components, and generates a fibrotic tissue image from the two images.

(Retardation Image)

The image of the high-birefringence region is obtained as follows. First, the image generation unit 147 generates a retardation image from the tomographic image data of the H- and V-polarized components. A value $\delta$ of a pixel of the retardation image is a quantified phase difference between the V- and H-polarized components in the position of the pixel included in the tomographic image and is calculated from the tomographic signals $A_H$ and $A_V$ using the following formula (3):

$$\delta = \arctan\left[\frac{A_V}{A_H}\right]. \qquad (3)$$

The calculation of the formula (3) is performed for each B-scan image to obtain a retardation image (also referred to as "tomographic image indicating a polarization phase difference"). By generation of the retardation image, it becomes possible to identify a layer with birefringence. Especially a structure that cannot be discriminated from a luminance tomographic image, such as fibrotic tissue, becomes obtainable.

Next, the high-birefringence region is obtained. A boundary of the region to be obtained is determined by, for example, specifying pixels with a larger amount of change in the retardation value in the depth direction than a predetermined threshold value. The amount of change in the depth direction can be calculated from a difference between the retardation values of two adjacent pixels of a pixel or from a gradient of the linear fitting of the retardation values of a plurality of adjacent pixels. Alternatively, the amount of change can be calculated from a gradient of a tangent line at a pixel which is obtained by differentiating the polynomial fitting of the retardation values of a plurality of adjacent pixels. Alternatively, the amount of change can be calculated by performing processing using a Sobel filter or Prewitt filter. In this way, the image of the high-birefringence region is obtained.

(Degree of Polarization Uniformity (DOPU) Image)

The image of the polarization-maintained region is obtained as follows. The image generation unit 147 calculates a Stokes vector S of each pixel from the obtained tomographic signals $A_H$ and $A_V$ and the phase difference $\Delta\Phi$ between the tomographic signals $A_H$ and $A_V$ using the following formula (4):

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\Phi \\ 2A_H A_V \sin\Delta\Phi \end{pmatrix}. \qquad (4)$$

The phase difference $\Delta\Phi$ is calculated using $\Delta\Phi=\Phi_V-\Phi_H$, where $\Phi_V$ and $\Phi_H$ are phases of a signal obtained in the calculation of two tomographic images. Next, a window of about 70 μm in the main scanning direction of the measurement light and about 18 μm in the depth direction is set to each B-scan image, and elements of the Stokes vectors calculated for the respective pixels in each window using the formula (4) are averaged. Then, a DOPU in the window is calculated using the following formula (5):

$$\text{DOPU}=\sqrt{Q_m^2+U_m^2+V_m^2} \qquad (5).$$

In the formula (5), $Q_m$, $U_m$, and $V_m$ are mean values of elements Q, U, and V of the Stokes vectors in the window. The above-described processing is performed with respect to every window in the B-scan image to generate a DOPU image (also referred to as "tomographic image which indicates a degree of polarization uniformity"). The DOPU is a numerical value which indicates polarization uniformity. In a region in which polarization is maintained, the numerical value of DOPU is close to one. On the other hand, in a region in which polarization is cancelled and not maintained, the numerical value of DOPU is smaller than one. In the inner structure of the retina, the retinal pigment epithelium has the property of cancelling the polarization state. Thus, a portion of the DOPU image that corresponds to the retinal pigment epithelium has a smaller value than the values of other regions. It becomes possible to obtain a structure that cannot be discriminated in the luminance tomographic image, especially the retinal pigment epithelium which becomes discontinuous due to a lesion. Next, threshold value processing (e.g., threshold value 0.75) is performed on the DOPU image to separate the polarization-maintained region and the polarization-cancelled region. In this way, the image of the polarization-maintained region is obtained. Examples of the polarization property image include the DOPU image based on the polarization cancellation information as well as an image based on the retardation information described above (retardation image), an image based on orientation information, and an image based on birefringence information. The images or information are part of three-dimensional polarization sensitive tomographic information.

(Fibrotic Tissue Image)

From the image of the high-birefringence region and the image of the polarization-maintained region obtained by the image generation unit 147 using the above-described method, the map generation unit 148 obtains, as an example of a lesion region, a region which has high birefringence and in which polarization is maintained, thereby generating a fibrotic tissue image f. In the fibrotic tissue image f, a pixel value set to the region which has high birefringence and in which polarization is maintained is different from pixel values set to other regions. For example, in a case in which the fibrotic tissue image f is an 8-bit unsigned image, a pixel value of 0 can be assigned to a region that is not fibrotic, and pixel values corresponding to respective fibrosis levels can be assigned to other regions. The fibrosis levels can be determined according to the degree of birefringence. While the method of obtaining the fibrotic tissue image using the tomographic image data of the H- and V-polarized components of any one frame among the tomographic image data of the polarization components of the m frames obtained by the repeated B-scans is described in the present exemplary embodiment, it is also possible to generate the fibrotic tissue image f using a tomographic image of polarization components of averaged m frames.

[Generation (Segmentation) of Layer Information]

In step S317, the map generation unit 148 generates (segments) retinal layer information from the luminance-averaged image r̄ generated in step S315 by the image generation unit 147.

Figure 4A:
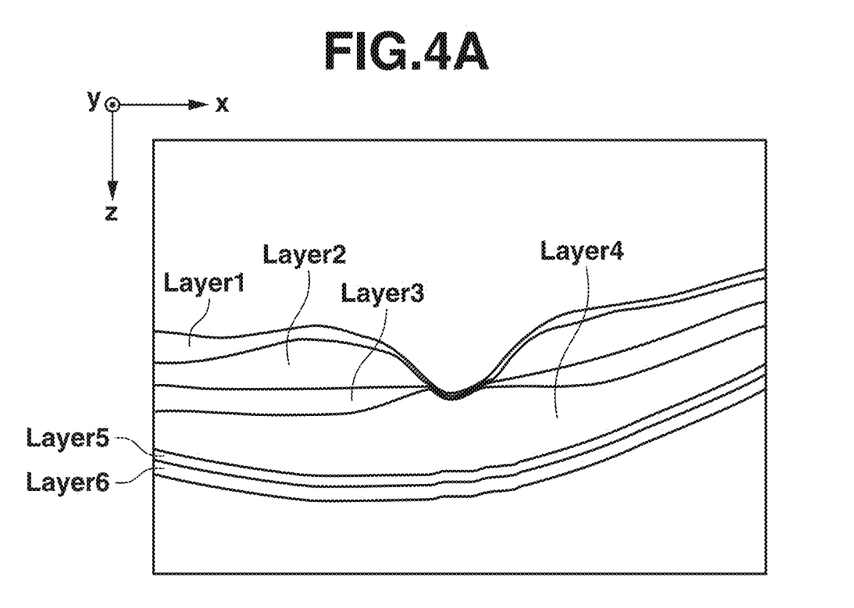
FIGS. 4A and 4B are diagrams each illustrating an example of a segmentation result according to an exemplary embodiment of the present invention.

The retina is known to include ten layers. In the present exemplary embodiment, some of the layers are combined to segment the layers into the following six layers as illustrated in FIG. 4A.

Layer 1: nerve fiber layer (NFL),
Layer 2: ganglion cell layer (GCL) and inner plexiform layer (IPL),
Layer 3: inner nuclear layer (INL) and outer plexiform layer (OPL),
Layer 4: outer nuclear layer (ONL) and external limiting membrane (ELM),
Layer 5: photoreceptor inner/outer segments (IS/OS), cone outer segment tip (COST), and retinal pigment epithelium (RPE), and
Layer 6: choriocapillaris (CC).

Next, the following describes a method of obtaining layer information l based on the luminance-averaged image r̄.

The map generation unit 148 applies a median filter and a Sobel filter to the tomographic image that is a processing target obtained from the luminance-averaged image r̄ to generate images (hereinafter, also referred to as "median image" and "Sobel image", respectively). Next, the map generation unit 148 generates a profile for each A-scan from the generated median image and the generated Sobel image. From the median image, a luminance value profile is generated. From the Sobel image, a gradient profile is generated. Then, the map generation unit 148 detects peaks in the profile generated from the Sobel image. By referring to the profile of the median image that corresponds to around or between the detected peaks, the boundaries of the respective regions of the retinal layer are obtained. As an exception, Layer 6 is segmented from the choroid side boundary of Layer 5 to a position corresponding to a predetermined distance including the choriocapillary layer, e.g., 10 μm.

Further, in the segmentation of Layer 5, the map generation unit 148 determines the boundary of RPE using the obtained DOPU image. RPE has the property of cancelling the polarization state due to melanocytes included in RPE, so a portion of the DOPU image that corresponds to RPE has a smaller value than other regions. Specifically, the DOPU image is a visual representation of the property derived from the structure of RPE, so even if RPE is deformed due to a disease, RPE can still be imaged more reliably than the cases of using changes in luminance alone.

Figure 4B:
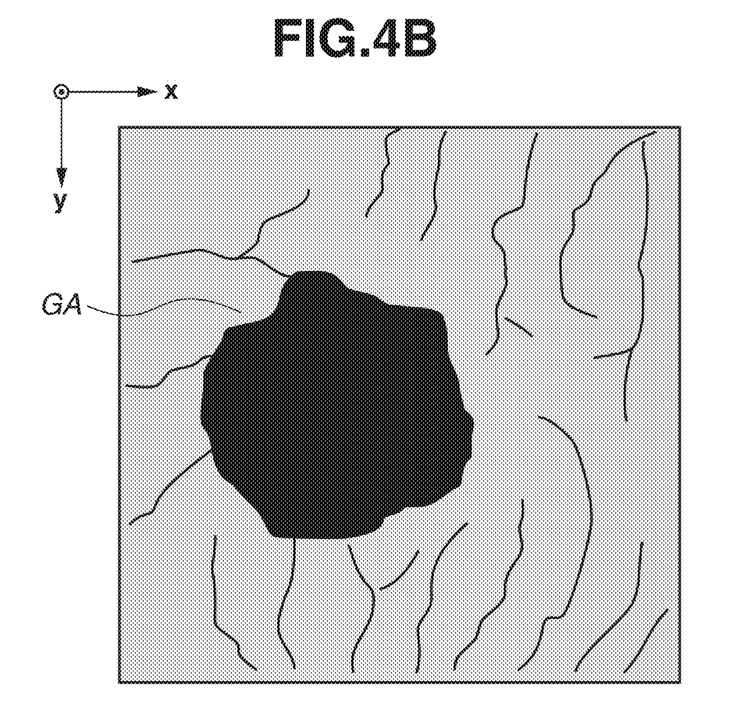

Further, the map generation unit 148 calculates the thickness of RPE from the determined boundaries of RPE, maps the calculated thickness, and stores the map as an RPE thickness map in an internal memory (not illustrated). FIG. 4B illustrates an example of the RPE thickness map, and the value of a pixel included in the map corresponds to a thickness of RPE. In the example, a region GA in a center of the map corresponds to a portion the thickness of which is decreased to zero because RPE is atrophied due to atrophic age-related macular degeneration.

[Generation of Blood Vessel Image (Motion Contrast)]

In step S318, the image generation unit 147 generates a blood vessel image from the luminance image.

First, the image generation unit 147 calculates a motion contrast. In the present exemplary embodiment, a variance value of signal intensity (luminance) is calculated for each pixel of the same position from the luminance images of the m frames output by the signal processing unit 144 in step S314, and the calculated variance values are determined as the motion contrast. Specifically, the image generation unit 147 calculates the motion contrast using corresponding pixel data of the plurality of pieces of calculated tomographic image data. Besides the variance value, any one of a standard deviation, difference value, decorrelation value, and correlation value can be used. Further, instead of the signal intensity, the phase can be used. Further, there are various methods for calculating the motion contrast, and as to the type of a feature amount of the motion contrast in the present exemplary embodiment, any index which indicates a change in luminance value of a pixel of the same Y position in the plurality of B-scan images is applicable. Further, the motion contrast can be calculated using a coefficient of variation normalized by a mean value of the same pixel in the respective frames instead of the variance value calculated for each pixel of the same position from the luminance images of the tomographic images of the m frames. The obtained motion contrast data is a part of three-dimensional motion contrast information described below.

Next, the image generation unit 147 performs motion contrast threshold value processing. The image generation unit 147 sets to zero the value of the motion contrast corresponding to a region with a luminance that is equal to or lower than the threshold value. By the threshold value processing, the motion contrast originating from a change in luminance by random noise is removed to reduce noise, and the blood vessels and other portions can be discriminated. The threshold value can be determined using the layer information obtained in step S317. The higher the threshold value is, the smaller the amount of noise becomes, but sensitivity of the motion contrast detection decreased. Thus, since the focus is on new blood vessels relating to RPE in the present exemplary embodiment, the noise threshold value of the motion contrast in the vicinity of RPE or choroid can be lowered. Further, smoothing processing can be performed before or after the threshold value processing. By the above-described processing, a blood vessel image b is generated.

[Generation of Volume Data]

In step S319, the signal processing unit 144 increments the index i of the position yi. In step S320, the signal processing unit 144 determines whether the index i is larger than the value of n. Specifically, whether the predetermined processing is performed at n places in all the y-positions is determined. If the signal processing unit 144 determines that the index i is not larger than the value of n (NO in step S320), the processing returns to steps S302 and S303. On the other hand, if the signal processing unit 144 determines that the index i is larger than the value of n (YES in step S320), the processing proceeds to step S321. After the above-described steps, a three-dimensional image is generated in the next step. Specifically, in step S321, the image generation unit 147 generates a three-dimensional luminance-averaged image $\bar{r}_{3D}$. In step S322, the image generation unit 147 generates a three-dimensional blood vessel image $b_{3D}$. In step S323, the image generation unit 147 generates a three-dimensional fibrotic tissue image $f_{3D}$. In this process, the number of independent fibrotic tissues is counted and recorded. Further, the volume of each of the fibrotic tissues is calculated. In step S324, the map generation unit 148 generates three-dimensional layer information $l_{3D}$.

Further, in step S325, the image generation unit 147 records the positions of blood vessels which extend across Layer 5 based on the three-dimensional blood vessel image $b_{3D}$ and the three-dimensional layer information $l_{3D}$. Further, the image generation unit 147 also records the positions of blood vessels near Layer 6 to Layer 5.

<Display Method>

In step S326, the three-dimensional luminance-averaged image $\bar{r}_{3D}$, the three-dimensional blood vessel image $b_{3D}$, the three-dimensional fibrotic tissue image $f_{3D}$, the three-dimensional layer information $l_{3D}$, the number of fibrotic tissues, the volumes of the respective fibrotic tissues, and the number of blood vessels near the layers, all of which are obtained in the above-described steps, are displayed on the display unit 146. Hereinafter, a set of the images and the information will be referred to as a data set. Examples of the display method are illustrated in FIGS. 5 and 6.

Figure 5:
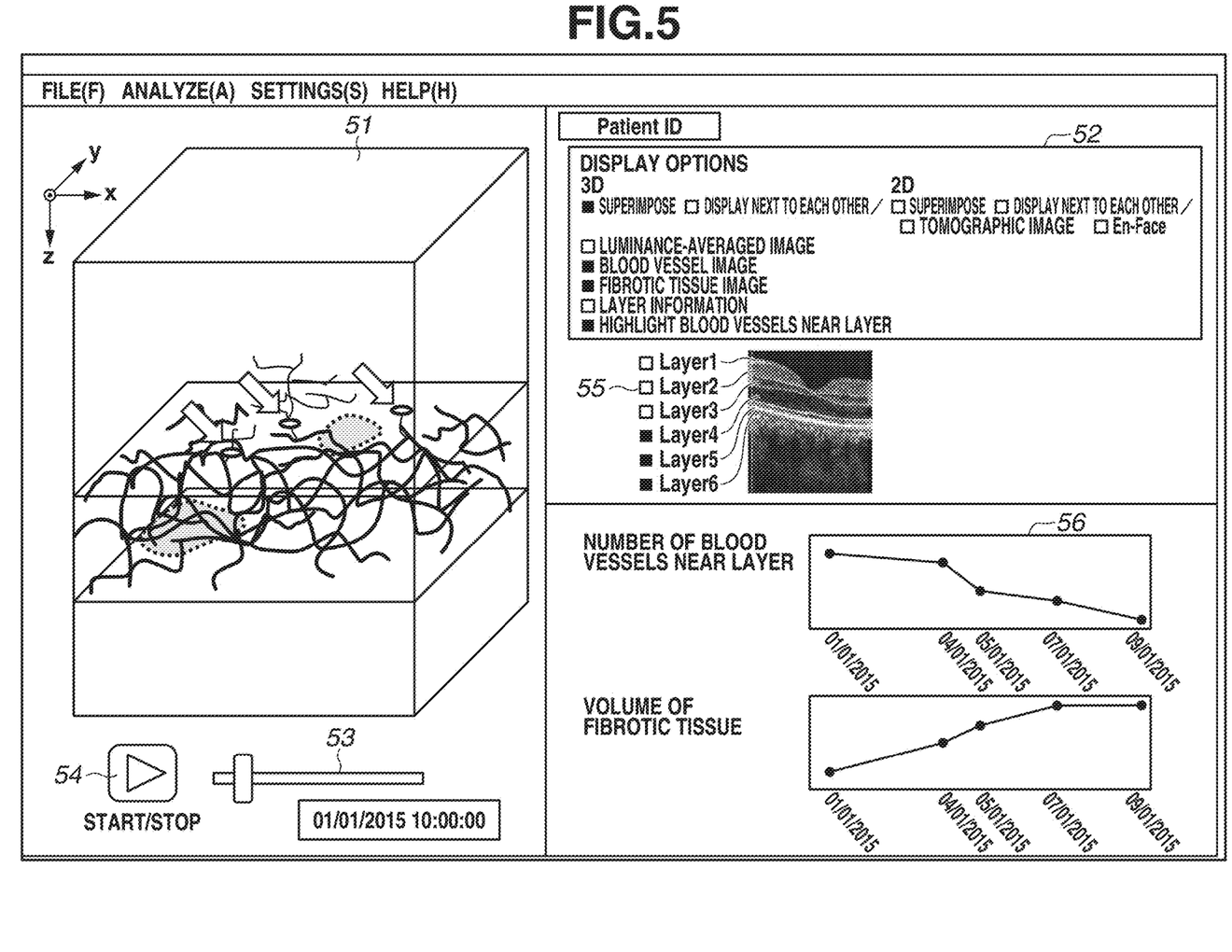
FIG. 5 is a diagram illustrating an example of a graphical user interface (GUI) according to an exemplary embodiment of the present invention.

In a display region 51 in FIG. 5, a combination or all of the three-dimensional luminance-averaged image $\bar{r}_{3D}$, the three-dimensional blood vessel image $b_{3D}$, the three-dimensional fibrotic tissue image $f_{3D}$, and the three-dimensional layer information $l_{3D}$ are superimposed and displayed. Further, the superimposition display can be switched to a display of data next to each other using a checkbox 52 located on a side of the image. The displayed three-dimensional image can freely be rotated, moved, enlarged, or reduced by an examiner operation, e.g., mouse operation, and the image can be viewed from any position and angle.

Figure 6:
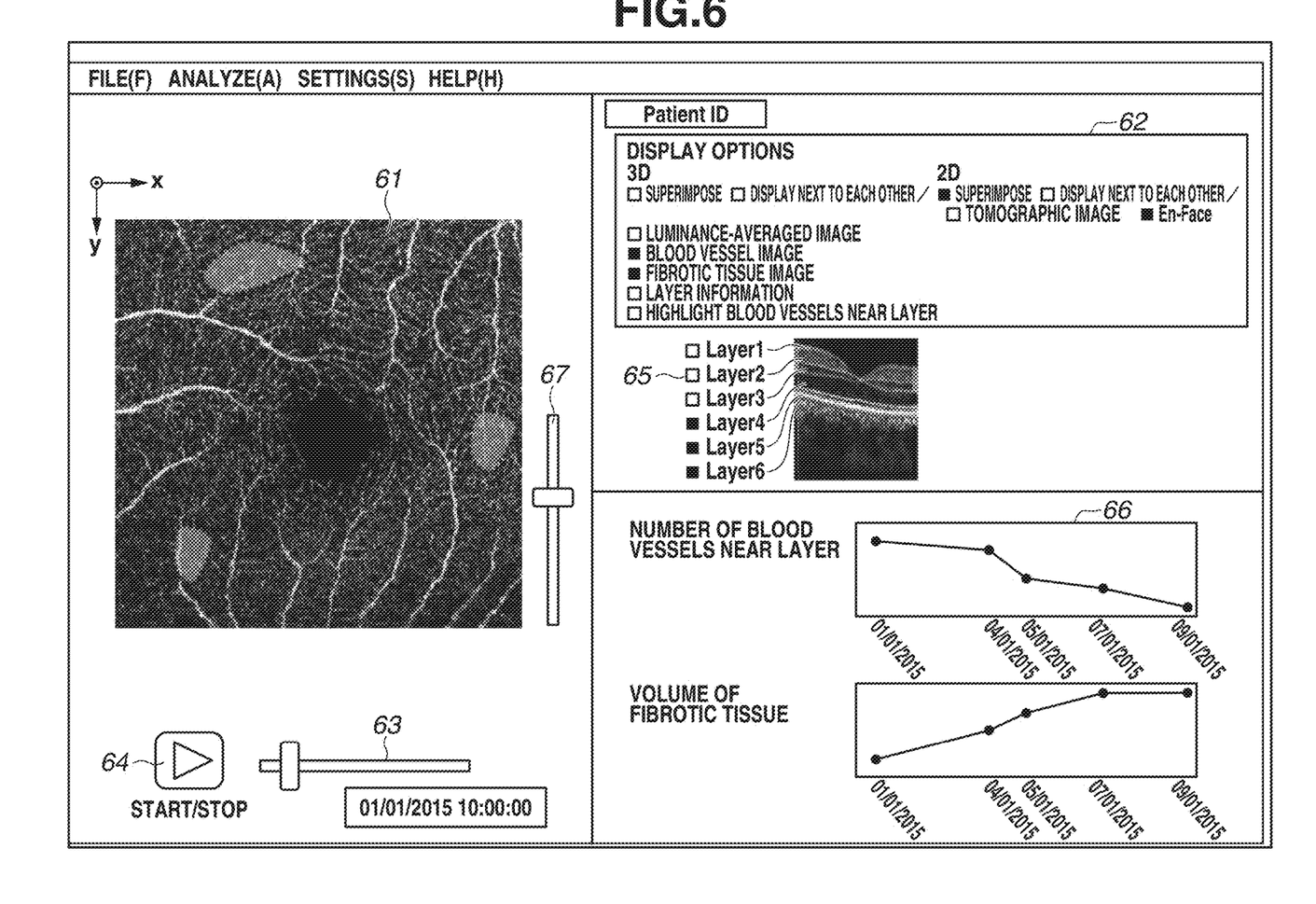
FIG. 6 is a diagram illustrating an example of a GUI according to an exemplary embodiment of the present invention.

Further, as illustrated in FIG. 6, the display of a display region 61 can be switched to a display of a two-dimensional tomographic image or en face image using a checkbox 62. FIG. 6 illustrates an example of an en face image on which the fibrotic tissue image (example of polarization en face image) and the blood vessel image (example of motion contrast en face image) are superimposed, and a fibrotic tissue region (shaded portion) is displayed on the blood vessel image. This makes it easier to identify the fibrosis region and the state of the blood vessels in the fibrosis region. As described above, when the en face image is selected according to an examiner operation, the en face image is generated using information on a layer selected in a checkbox 65. When the tomographic image is selected according to an examiner operation, a tomographic image of any position can be selected and displayed by operating a slide bar 67, and the tomographic images can be switched automatically and displayed sequentially like a slideshow by pressing a button 64. Even in the case in which the en face image is selected according to an examiner operation, the depth position of the en face image can be selected by operating the slide bar 67. Further, the checkboxes 62 and 65 are examples of determination means for determining a first region in a depth direction of a subject and a second region different from the first region. In this case, the determination means can be as follows: when the first region (e.g., near RPE) and the second region (e.g., near choroid) are determined, the determination may be made according to an examiner operation as in the present exemplary embodiment, or the first and second regions can be automatically determined according to a diagnostic purpose, etc. Further, when an examiner operates the checkbox 52 or 62 to change the images and information to be displayed on the display region 51 or 61, the images can be displayed in any combination of images and information on the display region 51 or 61. By the above-described configuration, the development of AMD and treatment effects can be checked efficiently.

For example, when the blood vessel image and the fibrotic tissue are selected to be displayed, the blood vessel image and the fibrotic tissue are displayed in the display region 51 or 61, and the locations and distributions of the blood vessels and the fibrotic tissue can be identified visually. An example is illustrated in FIG. 5. In FIG. 5, the three-dimensional blood vessel image $b_{3D}$ and the three-dimensional fibrotic tissue image $f_{3D}$ are superimposed and displayed as three-dimensional images in the display region 51. On the other hand, in FIG. 6, two types of images are superimposed and displayed as two-dimensional plane images. In both cases, a shaded portion indicates a region where fibrosis is developed in the fibrotic tissue image, and the blood vessels in the retinal layer and the portion where a tissue is degenerated by a disease can collectively be identified.

Further, as to a display target region, an image and information on a layer to be focused can be displayed alone in the display region 51 or 61 by selecting the layer to be displayed in the checkbox 55 or 65. In this way, in the case where the target disease is AMD, especially Layers 4 to 6 can be set as the display target, and new blood vessels, which are considered to emerge in the choroid and grow toward the inner layer of the retina, can be targeted and displayed.

Further, in the checkbox 52 or 62, highlighting and displaying the blood vessels near the layers can be selected. An example is illustrated in FIG. 5. FIG. 5 illustrates an example in which the blood vessels near the layers are highlighted with arrows. The highlighting can take various forms including the arrows. For example, a different color can be used. As described above, by combining the highlighting function of the blood vessels near the layers with the selecting of the display of the choroid and RPE layers in the checkbox 55 or 65, the new blood vessels relating to AMD can be identified visually with ease.

Further, the display unit 146 has a function of reading and displaying a previously measured and obtained data set of the same patient. A data set can be read and displayed when the examiner selects an examination number or an examination date. In the examples illustrated in FIGS. 5 and 6, the data set is switched by sliding a slide bar 53 or 63. Further, images can be switched and displayed automatically and sequentially in chronological order like a slide show at the press of a button 54 or 64. In this process, a selection on the checkbox 52, 62, 55, or is effective, and an image, site, and information on which an examiner focuses are displayed from the previous data set.

Further, in the display region 56 or 66, a graph based on the previous data set is displayed, with the vertical axis representing the number and volume of fibrotic tissues calculated in step S323 and the horizontal axis representing the time. The volume of fibrotic tissues can be selected from the volume of total fibrotic tissues included in an examination region and the volume of fibrotic tissues included in an examiner-selected region (e.g., volume of fibrotic tissue in selected layer). In FIGS. 5 and 6, the volume is calculated according to what is/are selected in the checkbox 52 or 62 and the checkbox 55, or 65. Similarly, a graph is displayed based on the previous data set, with the vertical axis representing the number, density, or length of the blood vessels extending across the layers and the blood vessels near the layers that are calculated in step 325 and the horizontal axis representing the time. The number, density, or length can be selected from the number, density, or length of the total blood vessels included in the examination region and the number, density, or length of the blood vessels included in an examiner-selected region (e.g., selected layer). In the example illustrated in FIGS. 5 and 6, the number is calculated according to what is/are selected in the checkbox 52 or 62 and the checkbox 55 or 65. The above-described graph is an example of a graph showing a change over time in a value of a parameter (e.g., number, volume) indicating a lesion region, such as a fibrotic tissue, and a graph showing a change over time in a value of a parameter (e.g., number, density) indicating a blood vessel. During a follow-up of exudative AMD involving new blood vessels, treatment with an anti-vascular endothelial growth factor (anti-VEGF), which reduces new blood vessel growth, is conducted, and it is considered that when the growth of new blood vessels or the bleeding from the new blood vessels is stopped, that portion is scarred and becomes fibrotic. In this case, a continuation of the treatment increases the burden on the patient but is not expected to produce a clinical effect, so it is important to stop the treatment based on objective grounds. By displaying in chronological order the volume of the blood vessel near the layers, which indicates new blood vessels to be treated, next to the volume of the region in which the lesion is inactivated as in the display region 56 or 66, the above-determination can be performed efficiently.

Figure 7:
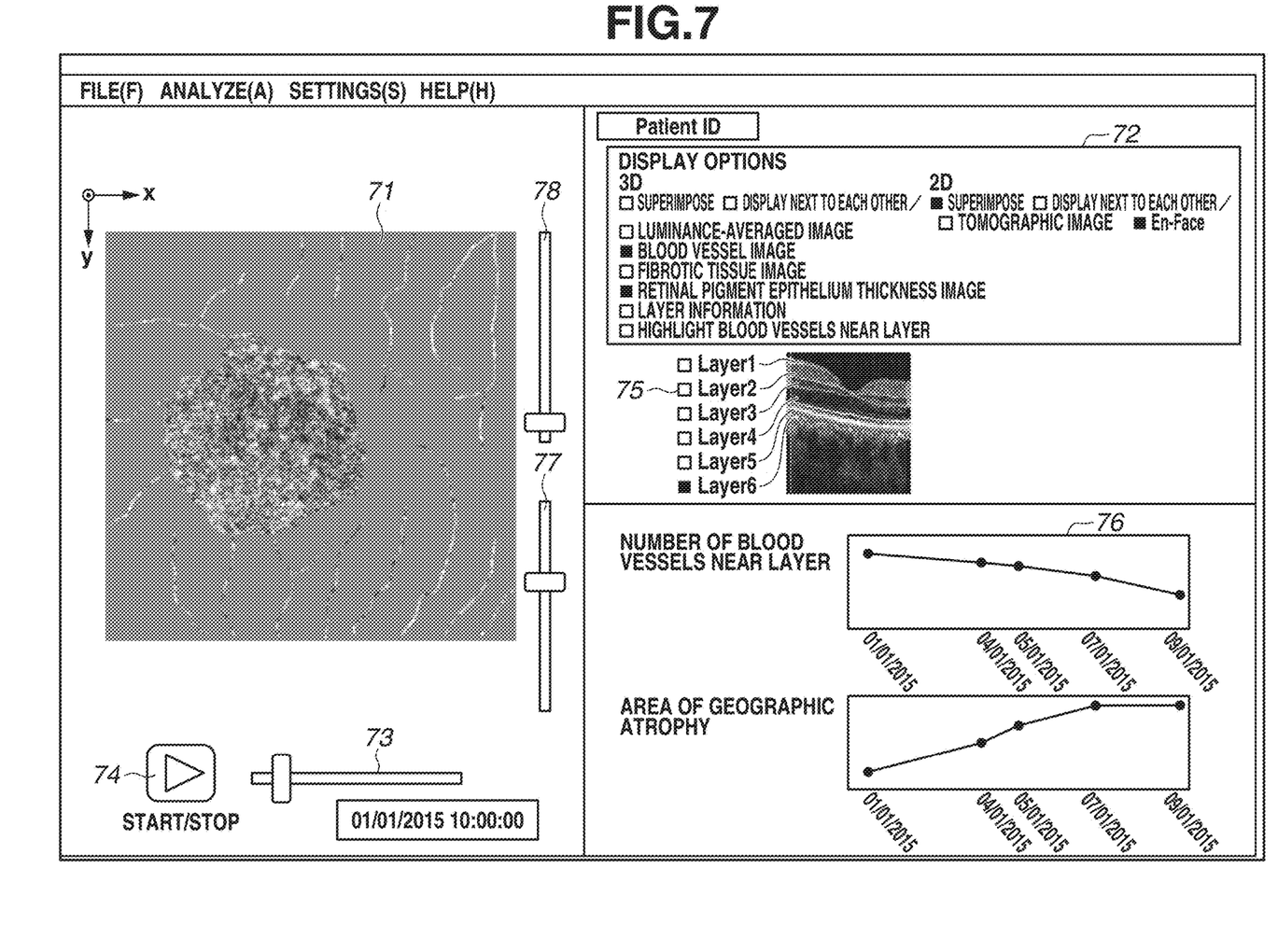
FIG. 7 is a diagram illustrating an example of a retinal pigment epithelium (RPE) thickness map and a blood vessel image which are superimposed and displayed according to an exemplary embodiment of the present invention.

Further, FIG. 7 illustrates an example in which the RPE thickness map and the blood vessel image described above are superimposed and displayed. In FIG. 7, display regions 71 to 77 are similar to the display regions 61 to 67 in FIG. 6, so description thereof is omitted. In the checkbox 72, the RPE thickness map ("retinal pigment epithelium thickness image" in FIG. 7) is added as a choice. By selecting the RPE thickness map and the blood vessel image, these two types of images are superimposed and displayed in the display region 71.

The images displayed on the display region 71 are images combined with the blood vessel image using the pixel values of the RPE thickness map as transmittance. In a region with the RPE thickness of zero, only the blood vessel image is displayed. Further, a slider 78 is for adjusting the relationship between the pixel values of the RPE thickness map and the transmittance. In FIG. 7, the RPE transmittance is set to the lowest condition. In this setting, the blood vessel image is visualized only when the RPE thickness is zero, and as the slider 78 is set upward, the transmittance gradually increases according to the value of the RPE thickness. Eventually, the blood vessel image becomes visible. In this way, the relationship between the state of the RPE atrophy region of AMD and the state of nearby blood vessels can be understood with ease.

Further, a target range (layer) of the blood vessel image displayed on the map generation unit 148 can be determined automatically from an image representing polarization characteristics of an eye to be examined. For example, the map generation unit 148 analyzes the fibrotic tissue image and the DOPU image, detects whether there is a fibrotic region and RPE atrophy region in the retina, and automatically checks the checkbox 55, 65, or 75 according to the detection result. In the region detection, a region with a higher pixel value of the fibrotic tissue image than a preset threshold value and a region with the RPE thickness equal to or smaller than a threshold value can be detected. The threshold values can be predetermined by analyzing a plurality of cases of related diseases.

The map generation unit 148 determines Layers 4, 5, and 6 as the display regions of the blood vessel image if a fibrosis region exists in the eye to be examined, or determines Layer 6 as the display region of the blood vessel image if RPE atrophy exists in the eye to be examined. Then, the map generation unit 148 automatically checks the checkboxes simultaneously with superimposing and displaying an image selected to be displayed at that point with the blood vessel image in the layer. Alternatively, the fibrotic tissue image can be selected if a fibrosis region exits, and the RPE thickness map can be selected if RPE atrophy is detected. In this way, the most relevant blood vessel region with respect to a lesion is automatically selected, and this significantly simplifies examiner operations. The relationship between the lesion and the layer to be targeted can be stored in advance in the map generation unit 148 such that the relationship can be changed. In this way, an appropriate layer can be selected according to pathological understanding.

As described above, according to the present exemplary embodiment, the image of the polarization characteristics of the eye to be examined and OCT angiography image are simultaneously presented so that the lesion is effectively displayed to enable efficient diagnosis.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-091607, filed Apr. 28, 2016, which is hereby incorporated by reference herein in its entirety.

What is claimed is:

1. An image processing apparatus comprising at least one processor, when executing a program, function as:
an information obtaining unit configured to obtain three-dimensional polarization sensitive tomographic information and three-dimensional motion contrast information of a subject based on tomographic signals of lights having different polarizations, the lights being obtained by splitting a combined light obtained by combining a returned light from the subject illuminated with a measurement light with a reference light corresponding to the measurement light;
a region obtaining unit configured to obtain a blood vessel region of the subject using the three-dimensional motion contrast information and to obtain a lesion region of the subject using the three-dimensional polarization sensitive tomographic information;
an image generation unit configured to generate at least one image in which the lesion region is superimposed on a motion contrast image generated using the three-dimensional motion contrast information or an image in which the blood vessel region is superimposed on a polarization image generated using the three-dimensional polarization sensitive tomographic information; and
a display control unit configured to cause a display unit to display the generated at least one image, a value of a parameter indicating the lesion region, and a value of a parameter indicating the blood vessel region.

2. The image processing apparatus according to claim 1, wherein the region obtaining unit obtains a three-dimensional lesion region of the subject using the three-dimensional polarization sensitive tomographic information, and
wherein the image generation unit generates a three-dimensional image in which the three-dimensional lesion region is superimposed on a three-dimensional image generated using the three-dimensional motion contrast information.

3. The image processing apparatus according to claim 2, wherein the image generation unit generates an en face image of a specific region of the subject using the three-dimensional image.

4. The image processing apparatus according to claim 1, wherein the region obtaining unit obtains a two-dimensional lesion region of the subject using the three-dimensional polarization sensitive tomographic information, and
wherein the image generation unit generates an image in which the two-dimensional lesion region is superimposed on a motion contrast en face image generated using the three-dimensional motion contrast information.

5. The image processing apparatus according to claim 1, wherein the display control unit cause the display unit to display a graph showing a change over time in a value of a parameter indicating the blood vessel region within a region selected by an examiner, the region being a corresponding region in each of a plurality of motion contrast images obtained at different examination dates and times selected by the examiner.

6. The image processing apparatus according to claim 1, wherein the display control unit causes the display unit to display a graph showing a change over time in a value of a parameter indicating the lesion region and a graph showing a change over time in a value of a parameter indicating the blood vessel.

7. The image processing apparatus according to claim 1, wherein the image processing apparatus is connected to and able to communicate with an imaging apparatus including a detection unit configured to detect the lights having different polarizations, and
wherein the information obtaining unit obtains the three-dimensional polarization sensitive tomographic information and the three-dimensional motion contrast information, based on the tomographic signals obtained, by the detection unit, by detection of the lights having different polarizations.

8. The image processing apparatus according to claim 1, wherein the subject is an eye to be examined and the information obtaining obtains the three-dimensional motion contrast information using a plurality of tomographic signals repeatedly obtained at the same position.

9. The image processing apparatus according to claim 1, wherein the image generation unit generates, as the polarization image, a polarization en face image of at least a part of a region of the subject in a depth direction thereof using the three-dimensional polarization sensitive tomographic information, and generates, as the motion contrast image, a motion contrast en face image of at least a part of a region of the subject in a depth direction thereof using the three-dimensional motion contrast information.

10. The image processing apparatus according to claim 9, wherein the processor further function as a determination unit configured to determine, as the at least a part of a region, at least one of a plurality of regions obtained by using a plurality of layers obtained by segmentation in accordance with an operation of an examiner.

11. An image processing apparatus comprising at least one processor, when executing a program, function as:
an information obtaining unit configured to obtain three-dimensional motion contrast information of a subject obtained using a tomographic signal of a combined light, the lights being obtained by splitting a combined light obtained by combining a returned light from the subject illuminated with a measurement light with a reference light corresponding to the measurement light;
a region obtaining unit configured to obtain a blood vessel region using the three-dimensional motion contrast information;
an image generation unit configured to generate a motion contrast image using the three-dimensional motion contrast information; and
a display control unit configured to cause a display unit to display the generated image and a graph showing a change over time in a value of a parameter indicating the blood vessel region.

12. The image processing apparatus according to claim 11,
wherein the information obtaining unit obtains the three-dimensional polarization sensitive tomographic information and the three-dimensional motion contrast information using tomographic signals of the lights having different polarization obtained by splitting the combined light,
wherein the image processing apparatus is connected to and able to communicate with an imaging apparatus including a detection unit configured to detect the lights having different polarizations, and
wherein the information obtaining unit obtains the three-dimensional polarization sensitive tomographic information and the three-dimensional motion contrast information using the tomographic signals obtained by detection of the lights having different polarizations by the detection unit.

13. The image processing apparatus according to claim 11, wherein the subject is an eye to be examined, and the information obtaining unit obtains the three-dimensional motion contrast information using a plurality of tomographic signals repeatedly obtained at a same position.

14. The image processing apparatus according to claim 11, wherein the display control unit causes the display unit to display a graph showing a change over time in a value of a parameter indicating the blood vessel region within a region selected by an examiner, the region being a corresponding region in each of a plurality of motion contrast images obtained at different examination dates and times selected by the examiner.

15. An image processing method comprising:
obtaining three-dimensional polarization sensitive tomographic information and three-dimensional motion contrast information of a subject based on tomographic signals of lights having different polarizations, the lights being obtained by splitting a combined light obtained by combining a returned light from the subject illuminated with a measurement light with a reference light corresponding to the measurement light;
obtaining a blood vessel region of the subject using the three-dimensional motion contrast information and to obtain a lesion region of the subject using the three-dimensional polarization sensitive tomographic information;
generating at least one image in which the lesion region is superimposed on a motion contrast image generated using the three-dimensional motion contrast information or an image in which the blood vessel region is superimposed on a polarization image generated using the three-dimensional polarization sensitive tomographic information, and
causing a display unit to display the generated at least one image, a value of a parameter indicating the lesion region, and a value of a parameter indicating the blood vessel region.

16. An image processing method comprising:
obtaining three-dimensional motion contrast information of a subject obtained using a tomographic signal of a combined light obtained by combining a returned light from the subject illuminated with a measurement light with a reference light corresponding to the measurement light;
obtaining a blood vessel region using the three-dimensional motion contrast information; and
generating a motion contrast image using the three-dimensional motion contrast information, and
causing a display unit to display the generated image and a graph showing a change over time in a value of a parameter indicating the blood vessel region.

17. A non-transitory computer-readable storage medium storing a program for causing a computer to execute steps in the method defined in claim 15.

18. A non-transitory computer-readable storage medium storing a program for causing a computer to execute steps in the method defined in claim 16.

* * * * *